Figure 1:
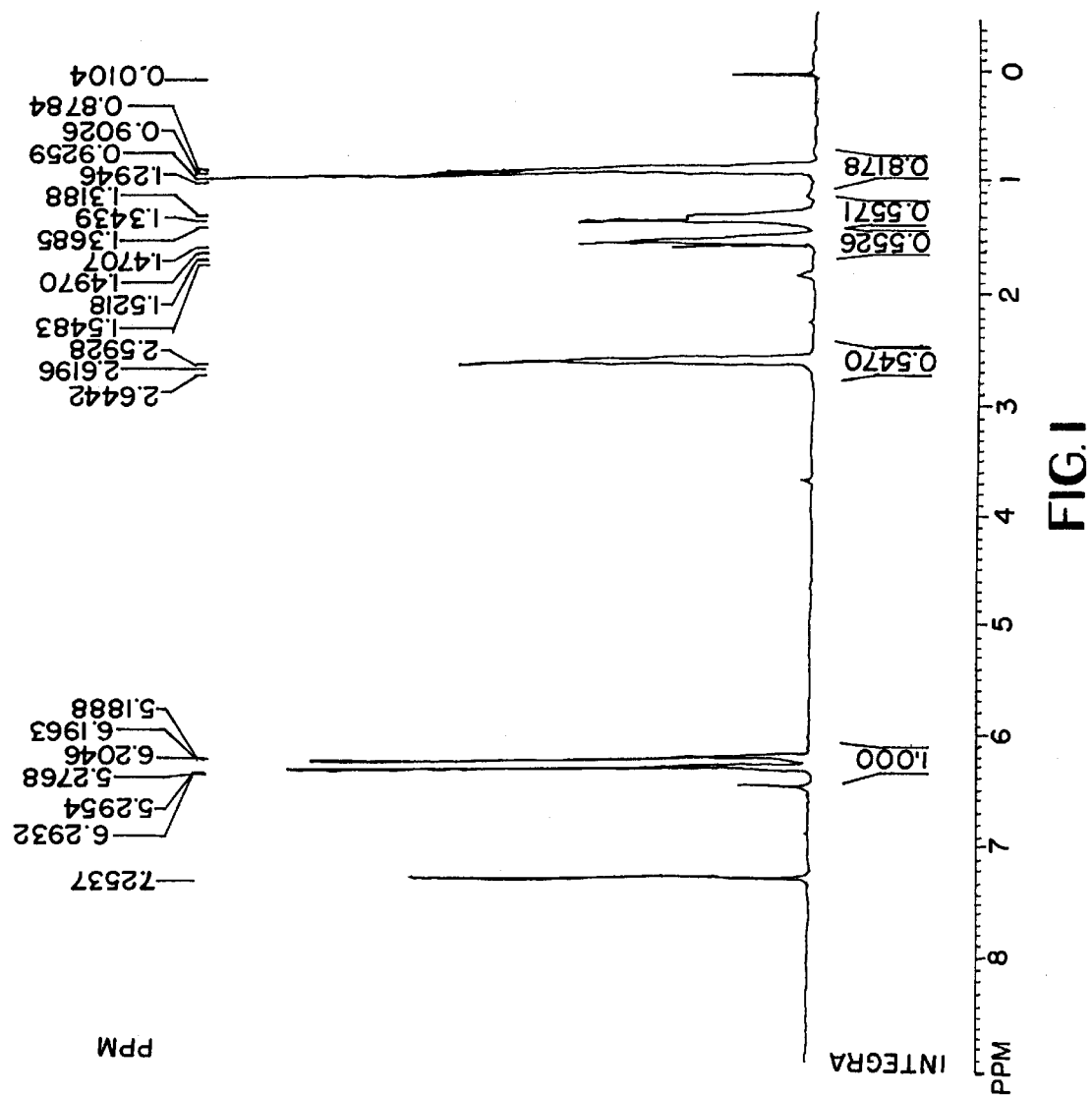

United States Patent [19]
Chen et al.

[11] Patent Number: 6,057,467
[45] Date of Patent: May 2, 2000

[54] METALLOCENE ADDUCT, ITS PREPARATION AND ITS APPLICATION IN OLEFIN POLYMERIZATION

[75] Inventors: Wei Chen; Ruen Wang; Zhenhua Jing; Weimin Wu; Zifang Guo; Xiaolan Shi; Lixin Zhang, all of Beijing, China

[73] Assignees: Research Institute of Petroleum Processing, SINOPEC; China Petrochemical Corp., both of Beijing, China

[21] Appl. No.: 09/307,186

[22] Filed: May 7, 1999

[30] Foreign Application Priority Data

Jul. 17, 1998 [CN] China .................. 98103034.3

[51] Int. Cl.[7] ............... C07F 17/00; C07F 7/00; C08F 4/64; B01J 31/00
[52] U.S. Cl. ............... 556/53; 556/11; 556/12; 502/103; 502/117; 526/127; 526/160; 526/173; 526/351; 526/352; 526/943
[58] Field of Search ............... 556/11, 12, 53; 502/103, 117; 526/127, 160, 173, 351, 352, 943

[56] References Cited

U.S. PATENT DOCUMENTS

| | | | |
|---|---|---|---|
| 5,001,205 | 3/1991 | Hoel | 526/128 |
| 5,200,537 | 4/1993 | Lee et al. | 556/11 |
| 5,336,795 | 8/1994 | Lisowsky | 556/56 |

FOREIGN PATENT DOCUMENTS

| | | |
|---|---|---|
| 1140720 | 1/1997 | China . |
| 0426643 | 5/1991 | European Pat. Off. . |
| 19627662 A1 | 1/1997 | Germany . |

*Primary Examiner*—Porfirio Nazario-Gonzalez
*Attorney, Agent, or Firm*—Birch, Stewart, Kolasch & Birch, LLP

[57] ABSTRACT

This invention relates to an three-constituent adduct of a metallocene.an ether.an metal halide having the general formula of $Cp'MQ_2 \cdot RXR' \cdot nM'Q_{2/n}$, where $Cp'$ is a substituted or an unsubstituted dicyclopentadienyl, M is zirconium or titanium, RXR' is tetrahydrofuran or diethylether, M' is alkali metal or alkali earth metal, n=1 or 2. The adduct can be exposed to air for several hours or stored in nitrogen atmosphere for a long period of time, which is prepared by means of a simple and convenient process without further separation and purification and used directly as a catalyst for polymerization of olefins.

16 Claims, 1 Drawing Sheet

METALLOCENE ADDUCT, ITS PREPARATION AND ITS APPLICATION IN OLEFIN POLYMERIZATION

FIELD OF THE INVENTION

This invention relates to a three-constituent adduct of metallocene, which consists of a metallocene compound, an ether and a metal halide, and a preparation process thereof. The adduct can be used as catalysts for the polymerization of olefins, especially for the homopolymerization of ethene and the copolymerization of ethene with an α-olefin. The present invention relates also to a catalyst system comprising the three-constituent adduct of metallocene as a main component of the catalyst, and a process of the homopolymerization or copolymerization of olefins by using the catalyst system.

BACKGROUND OF THE INVENTION

Generally, a process for synthesizing metallocene comprises converting cyclopentadiene or its derivative into an anion, complexing the resultant anion with a metal chloride, then separating and purifying the product to obtain a pure metallocene compound.

U.S. Pat. No. 5,200,537 discloses a process for preparing a metallocene having the general formula of $(RC_5H_4)_2MX_2$, wherein R is $C_1\sim C_{20}$ alkyl or silyl, M is zirconium or titanium, X is halogen. The process does not cost for refrigeration as it is carried out at room temperature, which comprises the preparation procedures of: (a) reacting $Na(C_5H_5)$ with RX(alkyl halide) in an organic solvent to form a mixture of $RC_5H_4$ and $C_5H_5$; (b) removing out the most of $C_5H_5$ by vacuum stripping at room temperature; (c) protonating the $RC_5H_4$ and (d) adding $TiCl_4$ or $ZrCl_4$ to form the metallocene compound, and then adding a solvent to separate out the pure metallocene compound. The yield is 56~74%.

In U.S. Pat. No. 5,336,795, a process is disclosed for preparing a transition metal complex compound having a mono-substituted cyclopentadiene ligand, wherein the mono-substituted cyclopentadiene ligand is prepared by using an oxide or hydroxide of alkali metal or alkali earth metal as a protonating agent, then the mono-substituted metallocene compound is formed by reacting the resultant ligand with a halide of transition metal elements.

In U.S. Pat. No. 5,001,205, a process for preparing a supported catalyst system of metallocene-aluminoxane is disclosed in detail, but no preparation process of the metallocene is given. The bridge-linked or noubridge-linked cyclopetadiene or a derivative thereof is used as a ligand of the metallocene, and is a pure metallocene compound. The aluminoxane used is methyl aluminoxane. The catalyst system is used for catalyzing the polymerization of ethene and of ethene with other α-olefins.

In EP 426,643 $A_1$, a process is disclosed in detail for preparing a isopropyl bridge-linked fluorenyl cyclopentadienyl zirconium dichloride. The process comprises two steps, (i), reacting butyl lithium or methyl lithium with a metallocene ligand in a polar solvent, e.g. tetrahydrofuran, then removing out the solvent to obtain a solid powder reactant; and (ii) reacting the solid powder reactant with $ZrCl_4$ powder at room temperature to carry out a solid-solid phase reactin in hexane, then removing out the solvent and washing the remainder to obtain a mixture of the isopropyl bridge-linked fluorenyl cyclopentadienyl zirconium dichloride and LiCl. The mixture can be used as a catalyst for preparing polypropylene. However, the mixture has poor stability and has to store in dry and oxygen-free conditions.

Furthermore, in CN 1 140 720A, a patent application of the present applicants, a composite metallocene catalyst with syndiotactic selectivity is disclosed. The catalyst prepared according to tile patent application is an three-constituent adduct of diphenylmethylene-(cyclopentadienyl-9-fluorenyl) zirconium dichloride.diethylether.lithium chloride having the expression of $Ph_2C[Cp-9-Flu]ZrCl_2.Et_2O.2LiCl$, which is used as a catalyst mainly for preparing syndiotactic polypropylene.

In regard to the preparation method of the metallocene catalyst used as a main catalyst component for the polymerization of olefins in the prior art, significant defects include: (1) many steps and complicated reactions are involved in the preparation process, thus not only a number of reactors are needed, but also the related reaction conditions are needed to be controlled severely; (2) complicated processes for the separation and purification are needed in the preparation methods, such as recrystallization and the like; (3) generally, the stability of the purified metallocene compound in air is poor, so it is not easy to be stored for a long term of time; (4) in general, the yield is about 60%, because of many reactions and separation steps. Even in the disclosed preparation process in CN 1,140,720A of the present applicants, a three-constituent adduct of $Ph_2C[Cp-9-Flu]ZrCl_2.Et_2O.2LiCl$ can be directly prepared and used as catalyst without any complicated separation and purification steps, it is only suitable for use as a catalyst for preparating syndiotactic polypropylene since the metallocene compound is of a bridge-linked type and its ligand has a large steric effect. When the metallocene adduct having syndiotactic selectivity, after having been supported, is used for catalyzing the polymerization of ethene, the usage amount of the cocatalyst used with the main catalyst component, methyl aluminoxane(MAO) is high. When the ratio of AL/Zr is at about 500, the catalytic activity is high, but when AL/Zr ratio is down to less than 200, the catalytic activity will be greatly decreased, thus the application of the adduct in polymerization of ethene largely restricted. Furthermore, since the process having several steps for preparating the metallocene ligand is complicated and the yield in each step is about 50%, the total yield based on the initial reactants is very low, when, for example, di-phenyl-fluorenyl-cyclopentadienyl methane is prepared.

Therefore, an object of the present invention is to provide a three-constituent adduct of metallocene with high stability on the basis of the prior art mentioned above, being able to he easily prepared, and having overcome defects of the prior art.

The second object of the invention is to provide a process for directly preparing the abovesaid adduct in high yield without the complicated steps of separating and purifying the metallocene compound.

DESCRIPTION OF THE INVENTION

The metallocene adduct provided according to the present invention is a three-constituent adduct of a metallocene—an ether—an metal halide having the general formula as the following:

$Cp'MQ_2.RXR'.nM'Q_{2/n}$ where Cp' is a metallocene ligand which is selected from an nonbridge-linked type of derived-dicyclopentadienyl; said derived-dicyclopentadienyl comprises cyclopentadienyl, indenyl or fluorenyl; the derived-dicyclopentadienyl in the ligand may be the same or different and may also include one or more substituted groups selected from $C_1\sim C_{12}$ alkyl, alkoxy, silyl, aryl or aralkoxy group.

Said metallocene ligand is preferably dicyclopentadienyl or substituted dicyclopentadienyl, the substituted group is preferably a $C_1$~$C_{12}$ alkyl most preferably, methyl, ethyl, propyl, isopropyl, butyl or isobutyl.

M is one of metal elements selected from Group IV B of the Period Table of Elements, preferably Zr or Ti, most preferably Zr.

Q is halogen, preferably chlorine.

RXR' is an ether or cyclic ether, R and R' may be the same or different and may be selected from $C_1$~$C_6$ alkyl; X is oxygen; preferably the ether is diethylether or tetrahydrofuran, more preferably tetrahydrofuran.

M' is selected from an alkali metal or alkali earth metal; preferably lithium or magnesium, most preferably lithium.

n=1 or 2, when the M' is alkali metal, n=2; when the M' is alkali earth metal, n=1; preferably n=2.

The term "adduct" is meant a new substance formed by the intermolecular forces between one and other kinds of substances when the crystal of one kind substance is forming and the other kind substance enters the crystal defects of said substance sequentially at the same time. Said metallocene adduct according to the invention is similar to this.

FIG. 1 is a spectrogram determined by $^1$H-NMR to the structure of the adduct according to the present invention.

The characteristic peaks of the RXR', δ1.787 and δ3.63 can be obviously observed in the determination of the adduct structure by $^1$H-NMR, which is the evidence of the existence of the adduct according to the present invention. Furthermore, when the adduct is extracted, with a solvent easily to dissolve the metallocene adduct, such as methyl dichloride and the like, the pure metallocene compound obtained by tile separation and recrystallization is extremely sensitive to air (especially when the metallocene containing fluorenyl or indenyl is synthesized). However, the three-constituent adduct is not sensitive to air and can be exposed in air for several hours or stored in nitrogen gas for a long period of time, when it is not separated and recrystallized but being used directly as a three component substance. This shows that the intermolecular forces exist among the three components in said adduct, by which the stability of the adduct is increased. Therefore, besides the components other than the metallocene stabilize the adduct, they will even have no unfavorable effect on the polymerization of olefins.

This invention relates also to provide a process for preparing directly the abovesaid three-constituent metallocene adduct in high yield, which need not carry out the complicated separation and purification of the metallocene compound.

The inventors have found that the three-constituent adduct of metallocene according to the invention can not be obtained by mixing directly the metallocene compound with the corresponding metal halide in an ether solvent, but the metallocene adduct according to the present invention can only be obtained after the preparation processes having the given reaction steps according to the present invention as said hereafter are used. This also shows the existence of the adduct of the present invention on another aspect.

We have found that the anion of the metallocene adduct ligand is formed in an ether solvent by the reaction of the cyclopentadienyl metallocene ligand compound with a strong basic protoning agent, and then the metallocene adduct is formed by adding a solid transition metal compound, for example $ZrCl_4$ or $TiCl_4$, under more moderate reaction conditions. The adduct is not needed to be separated and recrystallized, but needed only by removing most of solvent to form an adduct slurry, then adding an alkane to disperse the adduct slurry, which is then filtered and dried to obtain the metallocene adduct.

The preparation process of the metallocene adduct provided according to the invention comprises the steps of:

reacting the cyclopentadiene type of the metallocene ligand compound with a basic agent in an ether as a solvent at –10° C.~30° C., preferably at –5~ 10° C. to form a ligand anion; reacting the formed ligand anion with a metal halide having the general formula of $MQ_4$ at –78~30° C. to form the metallocene compound; while the metallocene is being formed, the metallocene adduct is formed from the metallocene and a metal halide having the formula of $M'Q_{2/n}$ released from the abovesaid reaction and the ether solvent; removing out preferably 50~98% of the solvent; adding an alkane to disperse the remainder, then filtering the resultant mixture and drying the remainder to obtain the solid product of the metallocene adduct.

In the preparation procedures, the cyclopentadiene type metallocene ligand compound comprises nonbridge-linked cyclopentadiene and derivatives thereof, such as fluorene or indene said cyclopentadiene and derivatives thereof may further comprise one or more substituted groups, preferably cyclopentadiene or mono-substituted cyclopentadiene; the substituted group is selected from the group consisting of $C_1$~$C_{12}$ alkyl, alkoxy, silyl, aryl or aralkoxyl, preferably, $C_1$~$C_{12}$ alkyl; more preferably, said cyclopentadiene type compound is cyclopentadiene, methyl-cyclopentadiene or butyl-cyclopentadiene. Said substituted cyclopentadiene is prepared by a well known process, for example, by a process through the reaction of an alkane halide with an excess amount of cyclopentadiene under the condition of phase-transfer catalysis.

Said ether solvent is an ether or cyclic ether having a general formula RXR', where R and R' may be the same or different which are $C_1$~$C_6$ alkyl, X is oxygen; preferably, the ether is diethylether or tetrahydrofuran, more preferably tetrahydrofuran.

Said basic agent is an organic compound of alkali metal or alkali earth metal, preferably alkyl lithium or aryl lithium, most preferably butyl lithium.

In said metal compound $MQ_4$, the M is optionally any one of elements selected from Group IVB of the Period Table of Elements, preferably zirconium or titanium, more preferably zirconium; Q is halogen, preferably chlorine.

Said alkane Is selected from $C_5$~$C_{12}$ alkane, preferably a petroleum ether with the boiling range of 60~90° C. The alkane is most preferably added in an amount of 1~10 times of the volume of the adduct slurry.

The invention relates also to a catalyst system for the homopolymerization or copolymerization of olefins, which comprises the abovesaid metallocene adduct as a main catalyst component, and methyl aluminoxane or the mixture of an alkyl aluminum with methyl aluminoxane as a cocatalyst, wherein the usage ratio of the cocatalyst to the main catalyst is in the range of 50–1000 based on the molar ratio of Al/M, preferably 100~500, more preferably 50–100.

A main advantage of the invention is that the provided metallocene adduct need not be separated, but can directly be used into the catalyst system for the homopolymerization or copolymerization of olefins, especially for the homopolymerization of ethene or copolymerization of ethene with other α-olefins. In the polymerization process, the homopolymerization or copolymerization of olefins is carried out by using the metallocene adduct provided according to the invention as a main catalyst component, and methyl aluminoxane or a mixture of alkyl aluminum and methyl aluminoxane, preferably the methylaluminoxane as cocatalyst under conditions sufficient to bring the olefins entering into the reaction. The cocatalyst may also be selected from one of the Lewis acids, for example an organo-boron compound. Said α-olefins are selected from $C_3$~$C_8$ α-olefins. The homopolymerization of olefin preferably is the homopolymerization of ethene. The copolymerization of olefins is preferably ethene with other α-olefins.

The polymerization reaction may be carried out by using well known processes in the art, preferably such as a solution polymerization process, slurry polymerization process or gas phase polymerization process. The solvent used in the solution polymerization or slurry polymerization may be an aromatic or an aliphatic hydrocarbon, for example, toluene or hexane and so on.

We have also found that when the metallocene adduct with nonbridge-linked dibutyl cyclopentadiene as a ligand, after having been supported, is used in catalytic polymerization of ethene, the usage amount of the methyl aluminoxane(MAO) is less, even the ratio of Al/Zr is in the range of about 50~100, the catalytic activity is still close to $10^8$ g PE/mol Zr. This demonstrates that the three-constituent metallocene adduct using the non-bridge-linked dibutyl cyclopentadiene as a ligand has significant and practical applicability in the regard with decreasing the cost of the catalyst.

The metallocene adduct provided according to the present invention has much higher stability than that according to the prior art, which can be exposed to air for several hours or stored in a nitrogen atmosphere for a long period of time. The preparation process of said adduct is easy and convenient in operation under a moderate condition, and the yield of the product obtained may be over 90% at most, for example, when the adduct is prepared on a kilogram scale, the reaction can be completed with the same reaction medium in the same reactor, and the reaction temperature may also be controlled by the same kind of heat-transfer medium in the reactor jacket, e.g. the mixture of glycol and water, and the adduct obtained need not be separated and purified, and can be directly used as the catalyst of olefin polymerization.

The following examples are intended to illustrate in detail the teaching according to the present invention but not limiting it in any way.

EXAMPLE 1

In this example, the adduct of dicyclopentadienyl titanium dichloride.tetrahydrofuran.lithium chloride having the expression,

$Cp_2TiCl_2.THF.2LiCl$ was prepared.

(a). Preparation of cyclopentadienyl lithium

Being cooled in an ice-water bath, a solution of 107 ml of butyl lithium(0.267 mol) in 2.5M hexane was slowly dripped to a solution of 17.6 g(0.267 mol) of cyclopentadiene(available from Aldrich Corp.) in 120 ml tetrahydrofuran (THF) under stirring, after the dripping is finished, the resultant mixture was continuously stirred for 1 hour, a white muddy solution of cyclopentadienyl lithium w as obtained.

(b). Preparation of metallocene adduct 25.5 g(0.134 mol) of $TiCl_4$ was added slowly to the resultant solution of the cyclopentadienyl lithium said above at −78° C. After the dripping was finished, the reaction mixture was continuously stirred overnight at room temperature, a dark-red muddy solution was then obtained. The solvent was removed out, the remainder was dispersed with 120 ml of a petroleum ether with the boiling range of 60~90° C., then filtered and dried. Eventually, 48.8 g of reddish-orange solid powder adduct was obtained.

Obvious characteristic peaks of THF, δ1.787 and δ3.63 can be observed in the adduct structure determined by $^1$H-NMR, seen in FIG. 1. The titanium content of the adduct determined by Inductive Coupling Plasma/Atomic Emission Spectrum (ICP/AES) was 10.91 wt %, the reaction yield was 83.0 wt % based on the titanium content.

EXAMPLE 2

In this example, the adduct of dicyclopentadienyl zirconium dichloride.tetrahydrofuran.lithium chloride having the expression,

$Cp_2ZrCl_2.THF.2LiCl$ was prepared.

(a). Preparation of cyclopentadienyl lithium

Being cooled in an ice-water bath, the solution of 47.3 ml of butyl lithium(0.118 mol) in 2.5M hexane was slowly dripped to a solution of 7.8 g(0.118 mol) of cyclopentadiene in 80 ml THF with stirring. After the dripping was finished, the resultant mixture was continuously stirred for 1 hour, a white muddy solution of cyclopentadienyl lithium was then obtained.

(b). Preparation of metallocene adduct 14.03 g (0.059 mol) of $ZrCl_4$ was added slowly to the abovesaid solution of the cyclopentadienyl lithium at −78° C. After dripping was finished, the resultant mixture was continuously stirred overnight at room temperature, a light yellow muddy solution was then obtained. 90% of the solvent was removed out, the remainder was dispersed with 80 ml of the petroleum ether, then filtered and dried. Eventually, 15.5 g of white solid powder adduct was obtained. The zirconium content of the adduct was 19.42 wt %, the reaction yield was 57.5 wt % based on the zirconium content.

EXAMPLE 3

In this example, the metallocene adduct of bis(methyl-cyclopentadienyl)titanium dichloride.tetrahydrofuran-.lithium chloride having the expression,

$(MeCp)_2 TiCl_2.THF.2LiCl$ was prepared.

(a). Preparation of methyl-cyclopentadienyl lithium

Being cooled in an ice-water bath, a solution of 15.2 ml of butyl lithium(0.038 mol) in 2.5M hexane was slowly dripped to the solution of 3.0 g(0.038 mol) of methylcyclopentadiene(Aldrich Corp.) in 50 ml THF. After the dripping was finished, the resultant mixture was continuously stirred for 1 hour, a white muddy solution of methyl-cyclopentadienyl lithium was then obtained.

(b). Preparation of metallocene adduct 3.6 g(0.019 mol) of $TiCl_4$ was added slowly to the resultant solution of methyl-cyclopentadienyl lithium said above at −28° C. After the dripping was completed, the resultant mixture was continuously stirred overnight at room temperature, a dark-yellow muddy solution was then obtained. 90% of the solvent was removed out, the remainder was dispersed with 50 ml of the petroleum ether, then filtered and dried. Eventually, 8.6 g of yellow solid powder adduct was obtained. The titanium content of the adduct was 8.99 wt %, the reaction yield was 85.0 wt % based on the titanium content.

EXAMPLE 4

In this example, the metallocene adduct of bis(methylcyclopentadienyl) zirconium dichloride.tetrahydrofuran.lithium chloride having the expression,

$(MeCp)_2ZrCl_2 \cdot THF \cdot 2LiCl$ was prepared.

(a). Preparation of methylcyclopentadienyl lithium

Being cooled in an ice-water bath, a solution of 51.5 ml of butyl lithium(0.0824 mol) in 1.6M hexane was slowly dripped to a solution of 6.5 g(0.0824 mol) of methylcyclopentadiene in 90 ml THF. After dripping was finished, the resultant mixture was continuously stirred for 1 hour, a milk white muddy solution of methylcyclopentadienyl lithium was then obtained.

(b). Preparation of metallocene adduct 6.0 g(0.0412 mol) of $ZrCl_4$ was slowly dripped to the resultant solution of methylcyclopentadienyl lithium said above at −78° C. After the dripping was completed, the resultant mixture was continuously stirred overnight at room temperature, a yellow muddy solution was then obtained. 70% of the solvent was removed out, the remainder was dispersed with 90 ml of the petroleum ether, then filtered and dried. Eventually, 7.8 g of yellow solid powder adduct was obtained. The zirconium content of the adduct was 20.40 wt %, the reaction yield was 42.5 wt % based on the zirconium content.

EXAMPLE 5

In this example, the metallocene adduct of bis(butylcyclopentadienyl) titanium dichloride.tetrahydrofuran.lithium chloride having the expression,

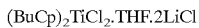
$(BuCp)_2TiCl_2 \cdot THF \cdot 2LiCl$ was prepared.

(a). Preparation of butylcyclopentadienyl lithium

Being cooled in an ice-water bath, a solution of 50.5 ml of butyl lithium(0.126 mol) in 2.5M hexane were slowly dripped to a solution of 15.4 g(0.126 mol) of butyl-cyclopentadiene(manufactured by RIPP) in 100 ml THF with stirring. After the dripping was finished, the resultant mixture was continuously stirred for 1 hour, a white muddy solution of butyl-cyclopentadienyl lithium was obtained.

(b). Preparation of metallocene adduct 12.0 g(0.063 mol) of $TiCl_4$ was added slowly to the resultant solution of butyl-cyclopentadienyl lithium said above at −78° C. After the dripping was completed, the resultant mixture was continuously stirred overnight at room temperature, a dark-red muddy solution was then obtained. 90% of the solvent was removed out, the remainder was dispersed with 100 ml of the petroleum ether, then filtered and dried. Eventually, 27.0 g of a brown solid powder adduct was obtained. The titanium content of the adduct was 9.05 wt %, the reaction yield was 81.0 wt % based on the titanium content.

EXAMPLE 6

In this example, the metallocene adduct of bis(butyl-cyclopentadienyl zirconium dichloride-tetrahydrofuran lithium chloride having the formula:

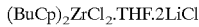
$(BuCp)_2ZrCl_2 \cdot THF \cdot 2LiCl$ was prepared.

(a). Preparation of butyl-cyclopentadienyl lithium

Being cooled in an ice-water bath, a solution 36.1 ml of butyl lithium(0.090 mol) in 2.5M hexane was slowly dripped to a solution of 11.0 g(0.090 mol) of butyl-cyclopentadiene in 100 ml THF with stirring. After the dripping was finished, the resultant mixture was continuously stirred for 1 hour, a white muddy solution of butyl-cyclopentadienyl lithium was then obtained.

(b). Preparation of metallocene adduct 10.7 g(0.045 mol) of $ZrCl_4$ was added slowly to the resultant solution of butyl-cyclopentadienyl lithium said above at −78° C. After the dripping was completed, the resultant mixture was continuously stirred overnight at room temperature, a yellow muddy solution was then obtained. 90% of the solvent was removed out, the remainder was dispersed with 100 ml of the petroleum ether, then filtered and dried. Eventually, 19.5 g of light yellow powder solid adduct was obtained. The zirconium content of the adduct was 9.05 wt %, the reaction yield was 81.0 wt % based on the zirconium content.

EXAMPLE 7

In this example, the metallocene adduct of bis(butyl-cyclopentadienyl zirconium dichloride.diethylether.lithium chloride having the expression,

$(BuCp)_2ZrCl_2 \cdot Et_2O \cdot 2LiCl$ was prepared.

(a). Preparation of butylcyclopentadienyl lithium

Being cooled in an ice-water bath, a solution of 49.8 ml of butyl lithium(0.125 mol) in 2.5M hexane was slowly dripped to a solution of 15.2 g(0.125 mol) of butyl-cyclopentadiene in 200 ml diethylether with stirring. After the dripping was finished, the resultant mixture was continuously stirred for 1 hour, a white muddy solution of butyl-cyclopentadienyl lithium was then obtained.

(b). Preparation of metallocene adduct 14.45 g(0.062 mol)of $ZrCl_4$ was added slowly to the resultant solution of butyl-cyclopentadienyl lithium said above at −78° C. After the dripping was completed, the resultant mixture was continuously stirred overnight at room temperature, a yellow muddy solution was then obtained. 80% of the solvent was removed out, the remainder was dispersed with 200 ml of the petroleum ether, then filtered and dried. Eventually, 20.8 g of light yellow solid powder adduct was obtained. The zirconium content of the adduct was 15.5%, the reaction yield was 57.0 wt % based on the zirconium content.

EXAMPLE 8

In this example, the metallocene adduct of bis(butyl-cyclopentadienyl zirconium dichloride.tetrahydrofuran.lithium chloride having the formula,

$(BuCp)_2ZrCl_2 \cdot THF \cdot 2LiCl$ was prepared.

(a). Preparation of butyl-cyclopentadienyl lithium

Being cooled in an ice-water bath, a solution 32.9 ml of butyl lithium(0.082 mol) in 2.5M hexane was slowly dripped to a solution of 10.0 g(0.082 mol) of butyl-cyclopentadiene in 100 ml THF with stirring. After the dripping was finished, the resultant mixture was continuously stirred for 1 hour, a white muddy solution of butyl-cyclopentadienyl lithium was then obtained.

(b). Preparation of metallocene adduct 9.75 g(0.041 mol) of $ZrCl_4$ was added slowly at 10° C. to the resultant solution of butyl-cyclopentadienyl lithium said above. After the dripping was completed, the resultant mixture was continuously stirred overnight at room temperature, a yellow muddy solution was then obtained. 90% of the solvent was removed out, the remainder as slurry was dispersed with 100 ml of the petroleum ether, then filtered and dried. Eventually, 18.0 g of light yellow powder solid adduct was obtained. The zirconium content of the adduct was 18.23 wt %, the reaction yield was 91.0 wt % based on the zirconium content.

EXAMPLE 9

In this example, the high pressure polymerization of ethene was carried out by using the metallocene adduct prepared according to the invention as the main catalyst and methylaluminoxane (MAO) as the cocatalyst.

1 liter of stainless steel reactor was evacuated and purged with a highly pure nitrogen for three times, then ethene gas was charged. A solution a polymerization of ethene was carried out by using toluene as the solvent, with a ratio of the metallocene adduct to methylaluminoxane (MAO) (available from Albemarble Corp. U.S.) was about 500. The reaction conditions included ethene pressure 0.7 MPa, temperature 50° C., stirring velocity 250 r.p.m., and the reaction time 1 hour. The product was discharged after the reaction was stopped, the polymerization product was precipitated with an acidic ethyl alcohol, then the resultant precipitate was washed, dried and weighed, and the activity of the metallocene adduct was calculated, the results are shown in Table 1.

EXAMPLE 10

In this example, a slurry homopolymerization process of ethene was carried out with the metallocene adduct according to the present invention, $(BuCp)_2ZrCl_2 \cdot THF \cdot 2LiCl$ as a main catalyst and methyl aluminoxane as a cocatalyst in a 2 liter—autoclave reactor, after the adduct was supported. In the 2 liter—stainless steel reactor, after the reactor being evacuated and purged with a highly pure nitrogen for three times, the ethene gas was filled, hexane was used as a solvent, the reaction was carried out at an Al/Zr molar ratio of 150 under conditions of 0.8 MPa pressure, 70° C. temperature with stirring. After the reaction was finished, the polymer was precipitated with an acidic ethanol, then the resultant precipitate was washed, dried and weighed. The activity of the metallocene adduct is $2.84 \times 10^7$ gPE/mol Zr.

EXAMPLE 11

In this example, a slurry copolymerization process of ethene and 1-hexene was carried out with the metallocene adduct according to the present invention, (BuCp)$_2$ZrCl2.THF.2LiCl as a main catalyst and methyl aluminoxane as a cocatalyst in a 3.2 $M^3$—autoclave reactor, after the adduct was supported. In the 3.2 $M^3$ reactor, hexane was used as a solvent, and the reaction was carried out at an Al/Zr molar ratio of 80 under the conditions of pressure 1.0 MPa and temperature 85° C. with stirring. After the reaction was finished, the resultant product was flashed, dried and weighed. The activity of the metallocene adduct is $5.0 \times 10^7$ gPE/mol Zr.

TABLE 1

| Ex. No. | Main catalyst | Co-catalyst | Activity of high pressure polymerization of ethene |
|---|---|---|---|
| 1 | $Cp_2TiCl_2 \cdot THF \cdot 2LiCl$ | MAO | $3.0 \times 10^5$ g PE/mol Ti.hr |
| 2 | $Cp_2ZrCl_2 \cdot THF \cdot 2LiCl$ | MAO | $0.8 \times 10^5$ g PE/mol Zr.hr |
| 3 | $(MCp)_2TiCl_2 \cdot THF \cdot 2LiCl$ | MAO | $1.5 \times 10^5$ g PE/mol Ti.hr |
| 4 | $(MCp)_2ZrCl_2 \cdot THF \cdot 2LiCl$ | MAO | $3.6 \times 10^5$ g PE/mol Zr.hr |
| 5 | $(BuCp)_2TiCl_2 \cdot THF \cdot 2LiCl$ | MAO | $0.8 \times 10^5$ g PE/mol Ti.hr |
| 6 | $(BuCp)_2ZrCl_2 \cdot THF \cdot 2LiCl$ | MAO | $7.6 \times 10^5$ g PE/mol Zr.hr |
| 7 | $(BuCp)_2ZrCl_2 \cdot Et_2O \cdot 2LiCl$ | MAO | $1.5 \times 10^5$ g PE/mol Zr.hr |
| 8 | $(BuCp)_2ZrCl_2 \cdot THF \cdot 2LiCl$ | MAO | $6.8 \times 10^5$ g PE/mol Zr.hr |

We claim:

1. A metallocene adduct consisting of a metallocene compound, an ether and a metal halide, wherein said adduct has a composition of the general formula as follows:

$$Cp'MQ_2 \cdot RXR' \cdot nM'Q_{2/n}$$

where Cp' is a metallocene ligand selected from a non-bridge-linked type of dicyclopentadiene-derivative group; said cyclodipentadiene-derivative group is selected from cyclopentadienyl, indenyl or fluorenyl; said cyclopentadiene-derivative group in the ligand may be the same or different, which may contain one or more substituents selected from $C_1$~$C_{12}$ alkyl, alkoxy, silyl, aryl or aralkoxy groups, M is one of the elements selected from Group IVB of the Period Table of Elements;

Q is selected from halogen;

RXR' is ether or cyclic ether, R and R' may be the same or different which is selected from alkyl of $C_3$~$C_6$, X is oxygen;

M' is selected from alkali metal or alkali earth metal;

n=1 or 2, when the M' is alkali metal, n=2; when the M' is alkali earth metal, n=1.

2. The adduct according to claim 1, wherein in said general formula:

Cp' is selected from dicyclopentadienyl or a substituted dicyclopentadienyl, the substituent may be the same or different, which is selected from $C_1$~$C_{12}$ alkyl;

M is selected from Zirconium or Titanium;

Q is chlorine;

RXR' is selected from tetrahydrofuran or diethylether;

M' is lithium;

n=2.

3. The adduct according to claim 1, wherein in said general formula:

Cp' is selected from dicyclopentadienyl having a mono-substituent selected from $C_1$~$C_{12}$ alkyl;

M is selected from Zirconium and Titanium;

Q is chlorine;

RXR' is selected from tetrahydrofuran;

M' is lithium;

n=2.

4. A process for preparing said adduct according to claim 1, comprising the steps of reacting an nonbridge-linked type of dicyclopentadienyl ligand compound with a basic agent in an ether as a solvent under −10~30° C. to form a ligand anion, reacting the ligand anion with a metal compound having the general formula $MQ_4$ at −78~30° C., then removing out the solvent, dispersing the remainder by adding an alkane, then filtering and drying; the definitions of said M and Q are the same as those in claim 1.

5. The process according to claim 4, Therein the nonbridge-linked type of dicyclopentadienyl compound is selected from cyclopentadiene or mono-substituted cyclopentadiene of $C_1$~$C_{12}$ alkyl.

6. The process according to claim 4, wherein said ether solvent is selected from tetrahydrofuran or diethylether.

7. The process according to claim 4, wherein said basic agent is selected from alkyl lithium.

8. The process according to claim 4, wherein said $MQ_4$ metal compound is selected from $TiCl_4$ or $ZrCl_4$.

9. The process according to claim 4, wherein 50~98% of the solvent are removed out after the reaction is completed, then the remainder is dispersed by adding an alkane which is selected from the group consisting of $C_5$~$C_{12}$ alkanes and a petroleum ether with boiling range of 60~90° C., and then filtered and dried.

10. A catalyst system for the homopolymerization or copolymerization of olefins, comprising the metallocene adduct according to claim 1 as a main catalyst component and methyl aluminoxane or a mixture of a alkyl aluminum compound with methyl aluminoxane as a cocatalyst, wherein the usage ratio of the cocatalyst to the main catalyst is 50~1000 based on the molar ratio of Al/M.

11. A catalyst system for the homopolymerization or copolymerization of olefins according to claim 10, wherein the usage ratio of the cocatalyst to the main catalyst is 50~500, based on the molar ratio of Al/M.

12. The catalyst system for the homopolymerization or copolymerization of olefins according to claim 10, wherein the usage ratio of the cocatalyst to the main catalyst is 50~200, based on the molar ratio of Al/M.

13. The catalyst system for the homopolymerization or copolymerization of olefins according to claim 10, wherein the usage ratio of the cocatalyst to the main catalyst is 50~100, based on the molar ratio of Al/M.

14. A process for the homopolymerization or copolymerization of olefins, wherein the process comprises that the homopolymerization or copolymerization of the olefin is carried out by using the catalyst system according to claim 10 under conditions sufficient for reacting the olefin.

15. The process according to claim 14, wherein said olefin is selected from ethene or $C_3$~$C_8$ α-olefins.

16. The process according to claim 14, wherein said homopolymerization of olefins is the polymerization of ethene and said copolymerization of olefins is the copolymerization of ethene with an $C_3$~$C_8$ α-olefin.

* * * * *